April 17, 1934. W. E. LENK Plant Pat. 93
GARDENIA PLANT
Filed Feb. 15, 1932
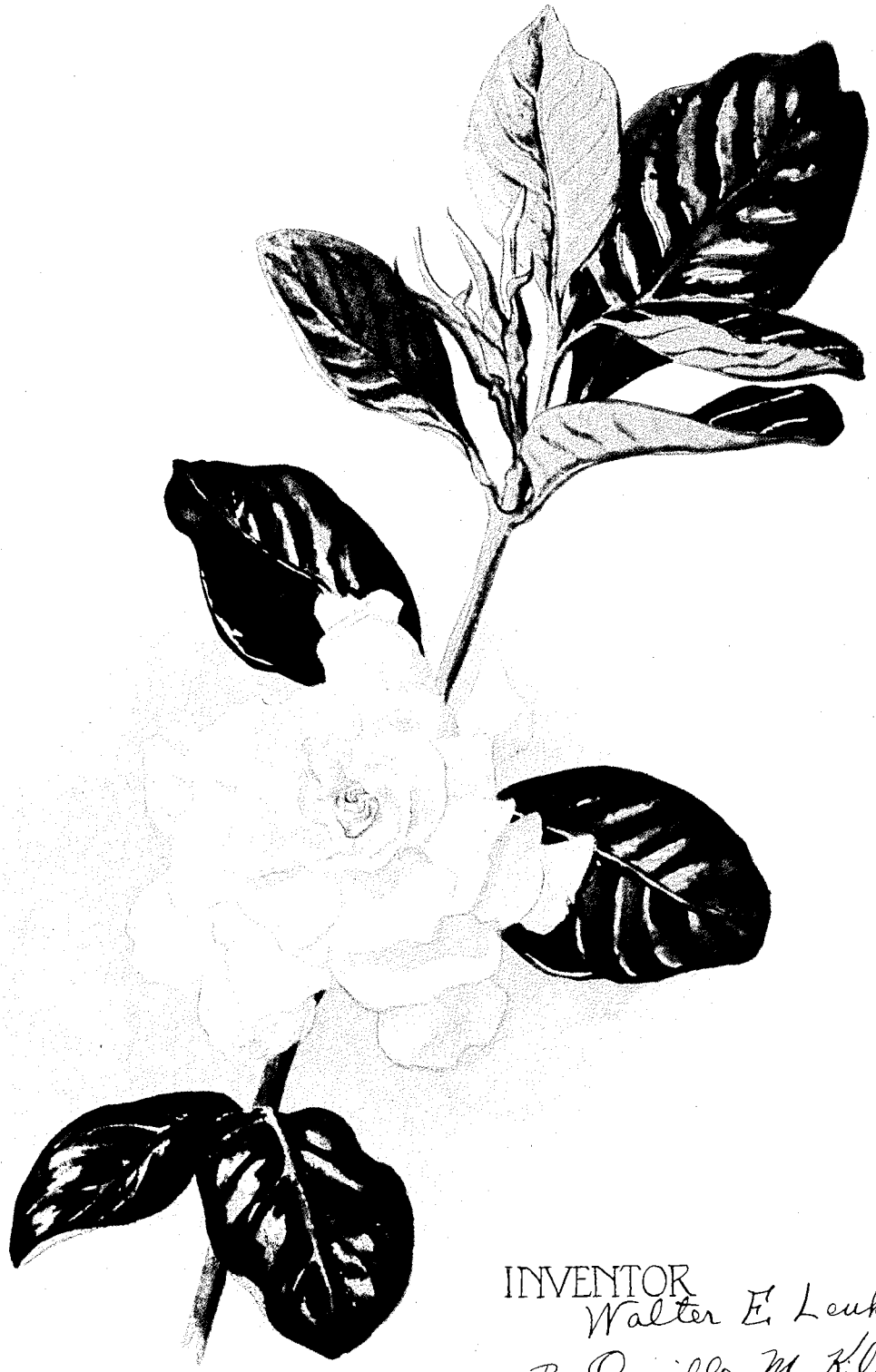
INVENTOR
Walter E. Lenk
By Orville M. Kile
PLANT PATENT AGENT Patented Apr. 17, 1934

Plant Pat. 93

UNITED STATES PATENT OFFICE

93

GARDENIA PLANT

Walter E. Lenk, Belmont, Mass.

Application February 15, 1932, Serial No. 593,188

1 Claim. (Cl. 47—60)

My invention relates to improvements in flowering gardenia plants of the general type grown in greenhouses in many parts of the United States. The object of my invention is to provide a new and distinct variety of gardenia plant of the type mentioned, having desirable and useful qualities not previously existing in any known single variety. More specifically stated, my invention consists in the production of a new and distinct variety of gardenia plant having large, glossy, pointed green leaves, being a vigorous grower free from disease, producing an extraordinary number of blossoms at all seasons of the year, and bearing flowers of extraordinary size and quality.

This new variety is a sport or mutation from the variety named "Grandiflora." On July 2, 1925, I purchased from the A. N. Pierson Company of Cromwell, Connecticut, more than one hundred plants of the Grandiflora variety and set them out in my greenhouse at Belmont, Massachusetts. The Grandiflora variety did not prove commercially satisfactory and has since been generally discarded by commercial growers. When this shipment of young gardenia plants developed, cuttings were made and rooted and the following year one of these new cuttings showed distinct differences in foliage and flowers. Subsequent observation showed that it had further differences in growing and flowering habits. This describes the origin of my new variety which I thus originated in 1926.

Several years were required to observe and test the various qualities of this new variety, to make certain that these qualities would reproduce, and then begin to accumulate a small stock of asexually propagated plants. Finally the superior commercial qualities of my variety having been fully demonstrated, I began to propagate on a larger scale and am now ready to sell plants to the public.

The accompanying illustration is a view in full color showing an opened blossom, together with a number of leaves and a partly developed bud.

The following is a detailed description of this gardenia plant or shrub and the buds and flowers produced by same:

The plant taken as typical of this variety when 16 months old and grown under good greenhouse conditions and producing blossoms, is about 22 inches in height and consists of numerous branches arising from a main stem, and these branches in turn producing side branches and offshoots. The plant is an evergreen. The plant has a tendency to throw off numerous side-shoots which produce flowers or which may be used for propagation. The variety is an extraordinarily heavy producer and can be propagated rapidly. If not pinched back this variety blooms almost continuously and readily adapts itself to maximum production of blossoms in the winter when they are most valuable.

Foliage; the leaves are large and magnolia-like, measuring 4 to 6 inches in length exclusive of the very short petiole. Two or 3 leaves are found at each whorl or "joint." Oftentimes these will alternate, first 2 leaves, then 3 leaves, then 2, etc., with sideshoots arising from the whorls having only two leaves. The distance between leaf whorls averages about 2¾ inches. The upper surface of each leaf is smooth and glistening and of approximately Empire green color as shown on Plate XXXII of Ridgeway's Color Standard and Nomenclature. The color is solid and even over the entire surface although the deep ribbing combined with the glistening effect causes the artist to show light areas in the painting. While the painting is artistically accurate in this respect it must be understood that the upper surface of the leaf is a uniform Empire green with the exception of a slightly lighter shade over the mid-rib and the side-ribs branching from the mid-rib. The under side of each leaf is minutely veined, not glistening, and of approximately a Biscay green color as shown on Plate XVII of Ridgeway's Color Standard and Nomenclature. Approximately this same color covers the entire visible stem and branch structure although the upper branches are somewhat lighter in color than the lower branches. The newer growths of leaves at the ends of the branches and on new shoots are several shades lighter in color than the mature leaves, being a Biscay green or even lighter on the upper surfaces as well as below.

The predominating shape of the ends of the leaves is pointed, although some of the newer leaves near the ends of flowering shoots have somewhat rounded ends. The edges of the leaves are smooth, there being no suggestion of serration, toothing, or hairy spines. The leaf curls but slightly.

Buds are usually 2 inches or more in length and ½ to ¾ inches in diameter just before beginning to unroll and burst into bloom. The long finger-like projections of the calyx develop far in advance of the bud and form an interesting feature of the plant when used as an ornamental shrub.

Blossoms are very large, usually measuring 4 to 5 inches across. The blossoms appear one after another on a given plant rather than many at one time. Seldom is there more than one prime blossom on a plant at any given time but when cut off, other blossoms follow in quick succession.

Eighteen to 26 large petals make up nine-tenths of the visible portion of the flower, but about 10 small petals are grouped in a tightly rolled arrangement in the center of the flower. The latter are ordinarily not visible until all the larger petals are fully folded back, which does not take place until the flower has passed its prime. These small central petals when finally disclosed have green tinted tops, even when the large petals in the outer whorl have turned quite yellow.

This group of tightly rolled small central petals encloses small imperfect but pollen-bearing anther-like structures (usually two) growing upon the surface of the innermost small petals.

The large petals have a thick leathery texture, are delicately veined and considerably curled. The appearance is velvety rather than waxy.

When the blossom is in its prime it is pure white in color, no yellow or green tints being visible. When on the plant the blossoms remain in this condition for four to six days before gradually assuming yellow tints on the outer petals, and after another three or four days the outer petals become quite yellow. To the ordinary observer the color of the flower in its prime is pure velvety white; the artist, however, sees certain shadows and tints not noted by the ordinary observer and the color illustration therefore shows a slight cream tint at points on the flower. It is to be noted, too, that the petals immediately surrounding the central group of very small pettals have opened back and disclose the greenish central group of petals which ordinarily would not be seen until the flower had ripened beyond its prime.

The petals instead of each being attached in the corolla tube separately, are attached to one another, or rather they merge into a single structure to form the tube. Thus the petals never "fall off" as is the case with most flowers when fading.

The flower of this new variety is exceptionally perfect in the unfolding and arrangement of its petals, giving the desired, flat, spreading effect to the outer petals and the high effect in the center.

The calyx is striking in structure. The tube is strongly ribbed and these ribs extend upward in the form of six long, tough fingers. These finger-like projections are 1 to 1¼ inches long and mature by the time the bud is only half grown. When the blossom finally opens, these long fingers serve a very useful purpose in supporting the outer petals in such a way that they lie "flat"—that is, perpendicular to the stem—and give a very pleasing effect. The average stem measures ½ inch from the point of attachment to the branch to the point where the flower when ripe detaches from the stem.

The odor of the blossom is distinct and fragrant but not of the intense, almost sickening quality characteristic of some gardenias.

The plant is a vigorous grower and quite resistant to disease.

The more important features which I believe distinguish my new gardenia plant from all other known varieties are:

First; the leaves are large, glistening and magnolia-like, ordinarily with pointed ends. The branches and main stem of the plant are green in color.

Second; the plant produces an abundance of flowers under greenhouse conditions in the vicinity of Boston, which is not true of a California variety which in California produces flowers of a size similar to my new variety. It adapts itself well to maximum winter blooming.

Third; the flowers are exceptionally large and perfect in form and of good lasting qualities. The color is pure write, as above described, and the petals are velvety rather than waxy. The odor is pleasant rather than excessive.

Fourth; the calyx is notably prominent and has six very long finger-like extensions which support the opened petals in pleasing form.

Fifth; the stem is of such a length and its method of attachment to the branch is such as to cause the blossom when cut to be displayed to best advantage.

Sixth; the plant is a vigorous grower, propagates rapidly and is resistant to disease.

I claim:

A variety of gardenia plant substantially as shown and described characterized particularly by its large, bright green leaves, its exceptionally large and perfect flowers of pure white color, its vigorous growing habits and maximum production of winter blossoms, and its resistance to plant diseases. WALTER E. LENK.